(12) United States Patent
Yang

(10) Patent No.: US 6,274,353 B1
(45) Date of Patent: Aug. 14, 2001

(54) METHOD AND COMPOSITIONS FOR IMPROVED POLYNUCLEOTIDE SYNTHESIS

(75) Inventor: Shuwei Yang, Rockville, MD (US)

(73) Assignee: Genecopoeia, Inc., Frederick, MD (US)

( * ) Notice: Subject to any disclaimer, the term of this patent is extended or adjusted under 35 U.S.C. 154(b) by 0 days.

(21) Appl. No.: 09/404,258

(22) Filed: Sep. 22, 1999

(51) Int. Cl.$^7$ .............................. C12P 19/34; C07H 21/00
(52) U.S. Cl. ...................... 435/91.2; 435/91.1; 536/25.3; 536/25.6
(58) Field of Search .............................. 435/6, 91.2, 91.1; 536/25.3, 25.6

(56) References Cited

U.S. PATENT DOCUMENTS

| 5,629,177 | 5/1997 | Hyman ................................ 435/91.2 |
| 5,939,257 | 8/1999 | Szasz et al. .............................. 435/6 |

OTHER PUBLICATIONS

Myers et al.:"Reverse Transcription and DNA Amplification by a Thermus thermophilus DNA Polymerase", *Biochemistry*, 30(31): 7661–7666 (1991).
Chou et al.: "Prevention of pre–PCR mis–priming and primer dimerization improves low–copy–number amplifications", *Nucleic Acids Research*, 20(7): 1717–1723 (1992).
D'Aquila et al.: "Maximizing sensitvity and specificity of PCR by preamplification heating", *Nucleic Acids Research*, 19(13): 3749 (1991.
Kellogg et al.: "TaqStart Antibody™: "Hot Start" PCR Facilitated by a Neutralizing Monoclonal Antibody Directed Against Taq DNA Polymerase", *Bio Techniques*, 16(6): 1134–1137 (1994).
Birch et al.: "Simplified hot start PCR", *Nature*, 381(6581): 445–446 (1996).
Silhavy et al.: "Uses of lac Fusions for the Study of Biological Problems", *Microbiological Reviews*, 398–418 (1985).
Gould et al.: "Firefly Luciferase as a Tool in Molecular and Cell Biology", *Analytical Biochemistry*, 175(1): 6–13 (1988).
Stewart et al.: Review Article–lax genes and the applications of bacterial bioluminescence, *Journal of General Microbiology*, 138(7): 1289–1300.
Misteli et al.: "Aplications of the green fluorescent protein in cell biology and biotechnology", *Nature Biotechnology*, 15: 961–963 (1997).
Cormack: "Green fluorescent protein as a reporter of transcription and protein localization in fungi", *Current Opinion in Microbiology*, 1(4): 406–410 (1998).
Ulmanen et al.: "Transcription and Translation of Foreign Genes in *Bacillus subtilis* by the Aid of a Secretion Vector", *Journal of Bacteriolgy*, 162(1) 176–1821(1985).
Ward et al.: "Construction and characterisation of a series of multi–copy promoter–probe plasmid vectors for Streptomyces using the aminoglycoside phosphotransferase gene from Tn5 as indicator", *MGG*, 468–478.
Glick et al.: "Factors affecting the expression of foreign proteins in *Escherichia coli*", *Journal of Industrial Microbiology*, 277–282 (1987).
Cenatiempo: "Prokaryotic gene expression in vitro: transcription—translation coupled systems", *Biochimie*, 68(4) 505–515 (1986).
Gottesman: "Bacterial Regulation: Global Regulatory Networks", *Annual Review of Genetics*, 18: 415–441 (1984).
Gold et al.: "Translational Initiation in Prokaryotes", *Annual Review of Microbiology*, 35: 365–403 (1981).
Richardson: "Bacteriophage T4 Polynucleotide Kinase", *The Enzymes, XIV*, Nucleic Acids, Part A,299–314 (1981).
Maunders: "Alkaline Phosphatase (EC 3.1.3.1)", *Methods in Molecular Biology*, 16, 331–341.
Yang et al.: "A eukaryotic enzyme that can disjoin dead–end covalent complexes between DNA and type I topoisomerases", *Proceedings of the National Academy of Sciences of the United States of America*, 93(21) 1996.
Jilani et al.: "Molecular Cloning of the Human Gene, PNKP, Encoding a Polynucleotide Kinase 3'–Phosphatase and Evidence for Its Role in Repair of DNA Strand Breaks Caused by Oxidative Damage", *The Journal of Biological Chemistry*, 274(34) 24176–24186 (1999).
Olivarse et al.: "The L1Tc, Long Interspersed Nucleotide Element from *Trypanosoma cruzi*, Encodes a Protein with 3'–Phosphatase and 3'–Phosphodiesterase Enzymatic Activities", *The Journal of Biological Chemistry*, 274(34) 23883–23886 (1999).
Yang et al.: "Fingerprinting of Near–homogeneous DNA Ligase I and II from Human Cells", *The Journal of Biological Chemistry*, 365(30)18130–18134 (1990).
Altschul et al.: "Gapped BLAST and PSI–BLAST: a new generation of protein database search programs", *Nucleic Acids Research*, 25(17), 3389–3402.

(List continued on next page.)

*Primary Examiner*—John S. Brusca
*Assistant Examiner*—Young J Kim
(74) *Attorney, Agent, or Firm*—Foley & Lardner

(57) ABSTRACT

The sensitivity and specificity of polynucleotide synthesis is increased by protecting the 3'-end of an oligonucleotide used as a primer in the synthesis of the polynucleotide. Protection of the 3'-end of an oligonucleotide prevents non-specific chain elongation. Removal of blocking group an elevated temperature, using a thermostable enzyme, permits template-specific polynucleotide synthesis. The present invention also provides oligonucleotides with a 3' end protected by a blocking group and a thermostable enzyme capable of removing the blocking group at an elevated temperature. The compositions and methods of the invention are very useful in a variety of techniques for DNA/RNA amplification and analysis, including medical genetics research and diagnosis, pathogen detection, forensic, and animal and plant genetics applications, among others.

15 Claims, 8 Drawing Sheets

OTHER PUBLICATIONS

Noya et al.: "The Multiple antigen blot assay (MABA): a simple immunoenzymatic technique for simultaneous screening of multiple antigens", *Immunology Letters,* 63(1) 1998.

Walenga et al.: Automation and Quality Control in the Coagulation Laboratory, *Clinics in Laboratory Medicine,* 14:4 709–729 (1994).

Kennedy et al.: "Protein–Protein Coupling Reactions and the Applications of Protein Conjugates", *Clinica Chimica Acta,* pp. 1–31.

Collins et al.: "The Molecular Genetics of Human Hemoglobin", *Progress in Nucleic Acid Research and Moecular Biology,* 31:315–463 (1984).

Ou et al.: "DNA Amplification for Direct Detection of HIV–1 in DNA of Peripheral Blook Mononuclear Cells", *Science,* 239 295–297 (1988).

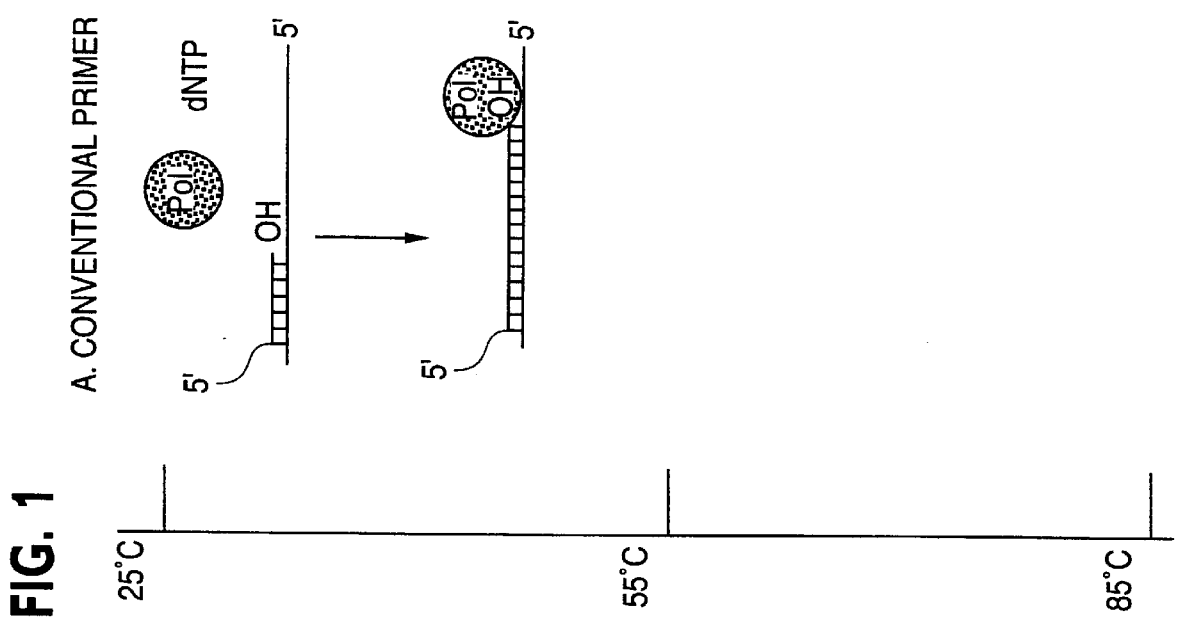
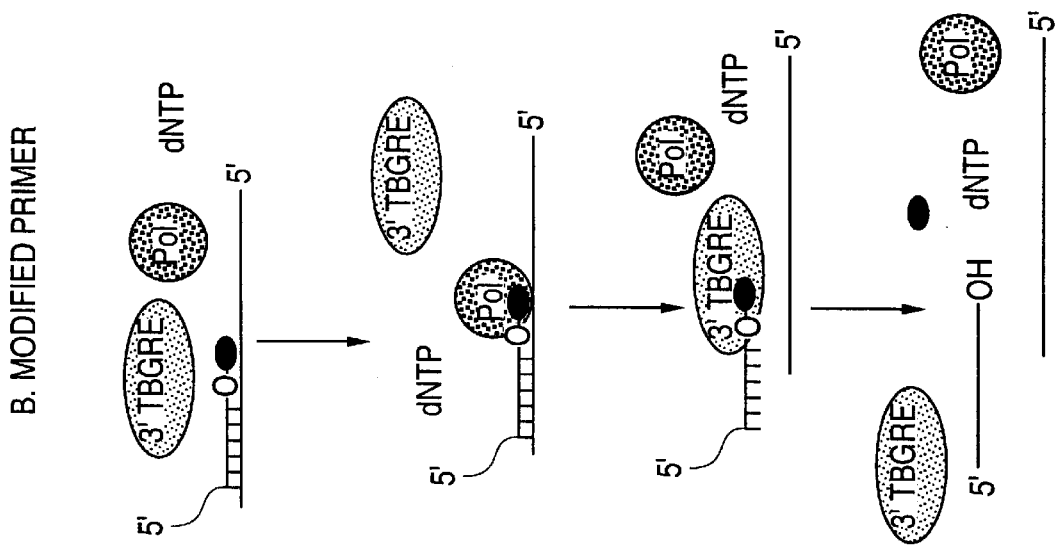
FIG. 1

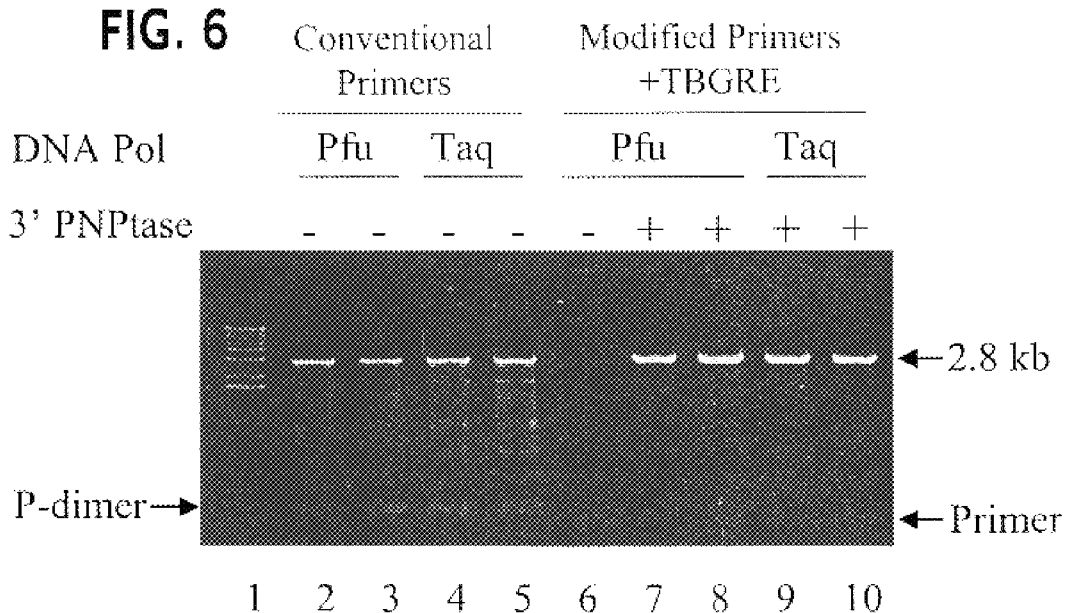

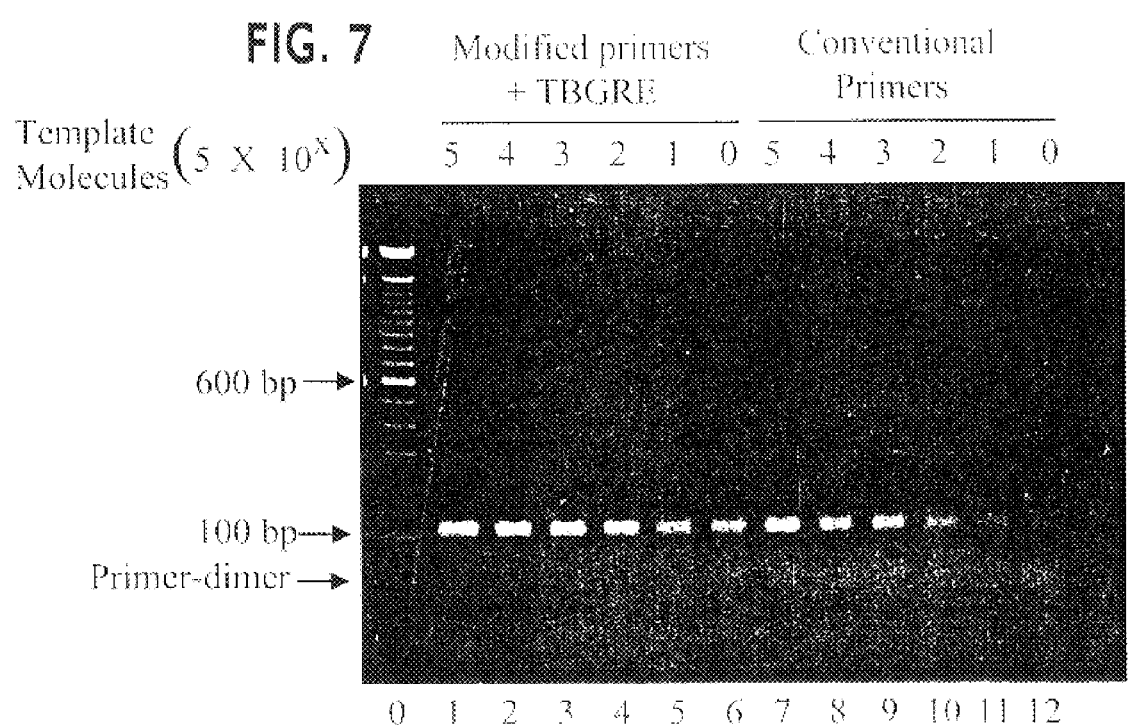

FIG. 8

```
Ph 1905          MFKIDRLRFGTAGIPISTPKPSTIAGIERVRELGLDAMELEFVRGINIKPELAKKIKYVA
Pfu 3'phosphatase MFKIDRLRFGTAGIPLSTPKPSTIAGIERVRELGLDAMELEFVRGINIKPELAKKIKYVA
Pab 1103         MFKIDRLRFGTAGIPISTPKPSTIAGIERVRELGLDAMELEFVRGVNIRPELAKKIKHVA
                 ************:.**************************:.**:.***.******:**

Ph 1905          EKNDIVLTAHAPYYINLNAKEKEKVEASKRRIIQSAERLYEAGGWSVVFHAGYYLKQPKE
Pfu 3'phosphatase KKNDVVLTAHAPYYINLNAKEKEKVESSKRRIIQSAERLYEAGGWSVVFHAGYYLKEHPE
Pab 1103         KKNDVVLTAHAPYYINLNAKEKEKVEASKRRIIQSAERLYEAGGWSLVFHAGYYLKQPPE
                 :***.***************************************:.*******:.  *

Ph 1905          SVYQKILSALKEIQKELMDKGIKVWLRPELTGKPTQFGDLKELVKLSQELELVLPAIDFA
Pfu 3'phosphatase KVYQKIESTLKDIERELKDRGIEVWLRPELTGKPTQFGDLKELIKLSQNLELVLPAIDFA
Pab 1103         LVYERIKSELKDIEKELLDRGIKVWIRPELTGKPTQFGNLMELIRLSQDLELVLPAIDFA
                  **::* *.***:**:** *::** **:***********:*:**::***:*********

Ph 1905          HAHARNKGKCNTEEEWREMLAIENELGREALDNMHIHISGIEYGEKGEKRHLNLEESDL
Pfu 3'phosphatase HAHARNKGKCNSEEEWREMLAIENELGREALDNMHIHISGIEYTEKGEKRHLNLEESDL
Pab 1103         HAHARNKGKCNSEEEWREMLTLIEKELGREALDNMHIHISGIEYSDKGEKRHLNLQESDM
                 ***********:********::**:******************::********:***:

Ph 1905          KWEDLLKVLKEFVKGVIISESPNIEGDAILMKKKWEELKI
Pfu 3'phosphatase KWEDLLKVLKEFVKGVIISESPNIEGDALLMKKKWEELKI
Pab 1103         RWEELLKTLKEFVKGVVISESPNIEGDAILMKKKWEELKI
                 :**:.***.*******:**********:***********
```

METHOD AND COMPOSITIONS FOR IMPROVED POLYNUCLEOTIDE SYNTHESIS

FIELD OF THE INVENTION

The invention relates to compositions and the methods for use in improving the sensitivity and specificity of polynucleotide synthesis. Specifically, the [inventive] method comprises protecting the 3'-end of an oligonucleotide used as a primer in the synthesis of a polynucleotide to prevent non-specific chain elongation [reaction], and removing the protection at an elevated temperature, using a thermostable enzyme, to allow template-specific polynucleotide synthesis. The present invention is also directed to a thermostable 3' polynucleotide phosphatase and its use as a marker protein. The present invention further relates to oligonucleotides with a 3' end protected by a blocking group. The instant invention also relates to methods for improving the sensitivity and specificity of amplification and analysis of DNA/RNA from a variety of samples. The compositions and methods of the invention are very useful in a variety of techniques for DNA/RNA amplification and analysis, including medical genetics research and diagnosis, pathogen detection, forensic, and animal and plant genetics applications, among others.

BACKGROUND OF THE INVENTION

Polynucleotide synthesis is a process of information transfer and usually requires another polynucleotide molecule as a template. In general, template-dependent polynucleotide synthesis involves the denaturing of the template polynucleotide molecule, the annealing of a primer molecule, and a step of chain extension whereby the 3' terminus of the primer is extended by a polynucleotide polymerase, using nucleoside-5'-triphosphate. This process is often repeated many times in vitro, such as in the case of a polymerase chain reaction (PCR).

Even though this information transfer process is remarkably accurate, the biomolecular machinery involved in the information transfer is not error-proof. These errors are a source of mutation in nature, and pose significant problems of infidelity for in vitro reactions such as PCR, random primer labeling, DNA sequencing, and reverse transcription. Both binding of primers to nonhomologous sites ("mispriming") and incorporation by the polynucleotide polymerase of incorrectly paired bases in the chain extension step are causes of the errors.

The availability of thermostable DNA polymerases which are stable at a temperature of up to 95° C., such as the Taq DNA polymerase isolated from the thermophilic bacterium *Thermus aquaticus* and Pfu DNA polymerase from the thermophilic archaebacterium *Pyrococcus furiosus* has improved the specificity and sensitivity of PCR by significantly reducing mispriming.

The isolation of Tth polymerase, a thermostable polymerase from *Thermus thermophilus* (Tth polymerase), that can function as both reverse transcriptase and DNA polymerase (Myers and Gelfand, *Biochemistry* 30:7662–7666 (1991)), has overcome the limitation of mesophilic viral reverse transcriptases which can only function at lower temperatures and which cannot "read through" the secondary structures of the RNA template at the low temperature. The reverse transcription performed at an elevated temperature using Tth polymerase eliminates secondary structures of template RNA, making the synthesis of full-length cDNA possible.

In most uses of PCR, the primer should bind very specifically to the target sites. While primer binding usually is very specific at elevated temperatures, the reaction mixture [,] must be held at lower temperatures (such as the ambient temperature) at certain stages of the PCR process, especially during the assembly of the reaction cocktail prior to the PCR temperature cycle. At lower temperatures, the primers may undesirably bind to the non-targeted nucleic acids, or to other primer molecules in the reaction mixture, resulting in nonspecific primer extension products and primer dimers, in addition to the specific product produced from the target nucleic acid. These undesired products cause high background, decrease amplification efficiency, and lower reaction specificity.

Despite recent progress in PCR technology, mispriming of background DNA and primer oligomerization still present a significant problem. This is especially true in diagnostic applications in which PCR is carried out in a milieu in which there are only a few copies of the target DNA (Chou et al. *Nucleic Acid Res.* 20:1717–1723 (1992)). It has been determined that non-specific chain extension by the DNA polymerase often occurs when all reactants have been mixed at ambient temperature, before thermal cycling is initiated, resulting in undesirable spurious amplification products.

Three methods have been reported which minimize these side reactions. The first method, termed "hot start" PCR, has various permutations, (Chou et al. Nucleic Acid Res. 20:1717–1723. (1992); D'Aquila et al. Nucleic Acid Res. 19:3749(1991)), with the common feature that all of the reagents are heated to 72° C. before a final reagent, usually the polymerase, is added to the reaction cocktail, preventing mispriming and primer oligomerization. Although this method does increase specificity, thereby reducing side products, the method is error-prone and tedious for dealing with a large number of samples, and the reaction mixture can become more easily contaminated.

In the second method, a polymerase-neutralizing antibody, for example, the Taq polymerase antibody sold under the tradename TaqStart Antibody, is added to the complete reaction mixture. This antibody inhibits the polymerase activity at ambient temperature (Kellogg et al. Biotechniques 16:1134–1137 (1994)), but is inactivated by heat denaturation once the reaction is thermocycled, releasing the active polymerase. The drawback of this approach is that the antibody needs to be stored at −20° C. until use, which means that detection kits need to be packaged and shipped in a controlled environment, adding to their cost. In addition, a significant amount of antibody (about 1 $\mu$g of antibody/5 U of Taq) is needed for a single PCR. The added antibody represents a significant amount of protein in the reaction mixture and interferes with further analysis of the PCR products by immunochemical assays such as ELISA.

In the third method, a modified form of Taq DNA polymerse, named AmpliTaq Gold, is employed in the PCR (Birch, D. E. et al. *Nature* 381:445–6 (1996)). The AmpliTaq Gold is inactive at room temperate and has to be heated to a temperature above 90° C. for at least 5 minutes in order to restore its activity. Therefore, a pre-PCR heating step at 95° C. is required. Although the AmpliTaq Gold can be activated during cycling and pre-PCR heat step can be eliminated, ten or more extra cycles are necessary to give equivalent product yield. Furthermore, many researchers find that it is difficult to amplify certain length of target sequence, for example 4 kb, from human genomic DNA by using Ampli-Taq Gold.

There is therefore a need in biotechnology and molecular biology for an improved method for improved specificity in polynucleotide polymerization with reduced mispriming and primer oligomerization.

Moreover, there is also a great need in biotechnology and molecular biology for markers that can be used to study gene expression, regulation and function. For example, the functional genomics project requires that the expression pattern of newly discovered genes be determined. Currently, several methods are available to monitor gene regulation and expression. These include the formation of fusion proteins with coding sequences for β-galactosidase and luciferases (Reviewed in T. J. Silhavy and J. R. Beckwith, Microbiol. Rev. 49:398 (1985); S. J. Gould and S. Subramani, *Anal. Biochem.* 175:5 (1988); and G. S. A. B. Stewart and P. Williams, *J. Gen. Microbiol.*, 138:1289 (1992)). Another protein that has been extensively used as a reporting marker in this field is the green fluorescent protein (reviewed by Misteli and Spector, *Nat Biotechnol.* 15(10):961–4 (1997); Cormack, *Curr Opin Microbiol* 1(4):406–10 (1998)). However, these enzymes are temperature sensitive and their assay have to be carried out in a short time period after sample preparation.

Similarly, current method utilizing these or similar enzymes for the determination of the presence and concentration of certain ligands also suffer the drawbacks discussed above, and there is a need for new methods utilizing enzymes whose activities are easily to assay and do not deteriorate rapidly at elevated temperatures.

SUMMARY OF THE INVENTION

It is an object of the instant invention to provide a composition comprising an oligonucleotide primer which has a 3' terminal hydroxy that is protected by a blocking-group. The 3'-end modified primer, according to the instant invention, prevents the chain-extension reaction by a DNA polymerase or a reverse transcriptase. Chain extension is even inhibited in the presence of all the necessary reaction components including dNTPs and metal cofactors.

The instant invention further provides a method for the addition of a nucleotide to a 3'-hydroxyl terminus of a preexisting polynucleotide molecule, comprising: (A). contacting a specimen suspected of containing a target polynucleotide molecule with a reaction mixture comprising (1) a primer complementary to said target polynucleotide molecule, wherein the 3'-hydroxyl terminus of the primer is protected with a blocking group that prevents chain-elongation; (2) a thermostable blocking group removing enzyme (TBGRE); (3) a thermostable polynucleotide polymerase, (3) at least one nucleoside-5'-triphosphate; and (B). elevating the temperature of the resulting mixture to higher than about 38° C., thereby generating a primer extension product. In a preferred embodiment, the instant method further comprises a step of (C) denaturing the primer extension product and conducting at least one additional primer extension reaction.

It is another object of the invention to provide a purified or recombinant thermostable 3'-polynucleotide phosphatase. The thermostable 3'-polynucleotide phosphatase according to the instant invention is capable of removing a 3' phosphate moiety of a 3' end modified primer only at a sufficiently high temperature. The removal of the 3' phosphate moiety allows the chain extension reaction to commence and continue only when the temperature of the reaction cocktail is sufficiently high, thus preventing non-specific amplification. Still further provided by the instant invention is a recombinant thermostable 3' polynucleotide phosphatase from Pfu.

This invention also relates to a method for producing a recombinant thermostable 3' polynucleotide phosphatase that is derived from a hyperthermophilic archaebacteriumm *P. furiosus*.

The present invention also relates to using the thermostable 3'-phosphatase as a marker protein. For example, this invention relates to a method for quickly determining whether an in vitro expression system successfully expresses the target protein, the method comprising (1) fusing a DNA molecule having DNA sequence encoding the protein of interest to the DNA sequence encoding a thermostable 3' phosphatase activity such that the protein produced by the DNA molecule will have the protein of interest fused to the 3' phosphatase of the invention; (2) placing the fusion gene in a suitable expression vector; (3) expressing the fused-DNA molecule; (4) heating the expressing cells to a temperature of 70° C.; and (5) detecting the thermostable 3'-phosphatase activity.

BRIEF DESCRIPTION OF THE DRAWINGS

FIG. 1 is a schematic diagram illustrating an exemplary method for improving PCR specificity and sensitivity. (A). The extension of the conventional primer, which is mis-annealed to the non-target DNA sequence, by DNA polymerase (indicated by Pol.) occurs in the PCR at low temperature. The newly synthesized DNA can serve as a template in the following cycles, causing high background and low yield of specific products. (B). When a modified primer with a blocker at its 3' end is used in PCR the 3' blocker prevents the extension of the mis-annealed primer at low temperature, while the Thermosatble Blocker Group Remove Enzyme (3'TBGRE) specifically and efficiently removes the 3' blocker at temperature above 55° C., converting modified primer to conventional primer for DNA synthesis by DNA polymerase in the following cycles. The combination of the functions of modified primer and the 3' will increase the specificity and sensitivity of PCR and PCR related techniques. The temperatures at which these events occur are indicated in the left by a vertical bar.

FIG. 6 is a photograph of an agarose gel showing a comparison between the PCR products (a 2.8 kb fragment of the β-globin gene amplified by the Taq and Pfu DNA polymerase) using modified primers plus the *P. furiosus* 3'-polynucleotide phosphatase and conventional primers, from 50 ng of human genomic DNA. Lane 1 is the 1 kb DNA molecular weight marker (Life Technologies), Lanes 2, 3, 4, and 5 are the PCR products with a pair of conventional primers; the samples in these lanes contained significant amount of non-specific products and primer dimers ("P-dimer"). Lanes 6, 7, 8, 9, and 10 are the PCR products with a pair of primers modified at the 3' end plus a 3' TBGRE (the *P. furiosus* 3' polynucleotide phosphatase).

FIG. 7 is a photograph of an agarose gel showing a comparison between the PCR products (a 115 bp fragment of the HIV gag gene by Taq DNA polymerase) using the modified primers plus a TBGRE (the *P. furiosus* 3' polynucleotide phosphatase) and the conventional primers. Lane 0 is the 100 bp DNA molecular weight marker (Life Technologies). As described in Example 10, lanes 1, 2, 3, 4, 5, and 6 are the PCR products with a pair of primers modified at the 3' end plus the 3' polynucleotide phosphatase. Lanes 7, 8, 9, 10, 11, and 12 are the PCR products with a pair of conventional primers. All PCR used 200 ng of human genomic DNA as template. The DNA molecules of the template of the HIV gag gene used in the PCR reactions were indicated on the top of the figure.

FIG. 8 shows the Amino acid sequences alignment of the polypeptide deduced from the gene (SEQ ID NO:6) of *P. furiosus* 3' polynucleotide phophatase gene and the hypothetical open reading frames of Ph 1905 (SEQ ID NO:16) from *P. horikoshii* and Pab 1103 (SEQ ID NO:17) from *P. abysii*. The (*) indicates identity and (:) indicates similarity.

DETAILED DESCRIPTION OF THE INVENTION

Definitions

Figure 2:
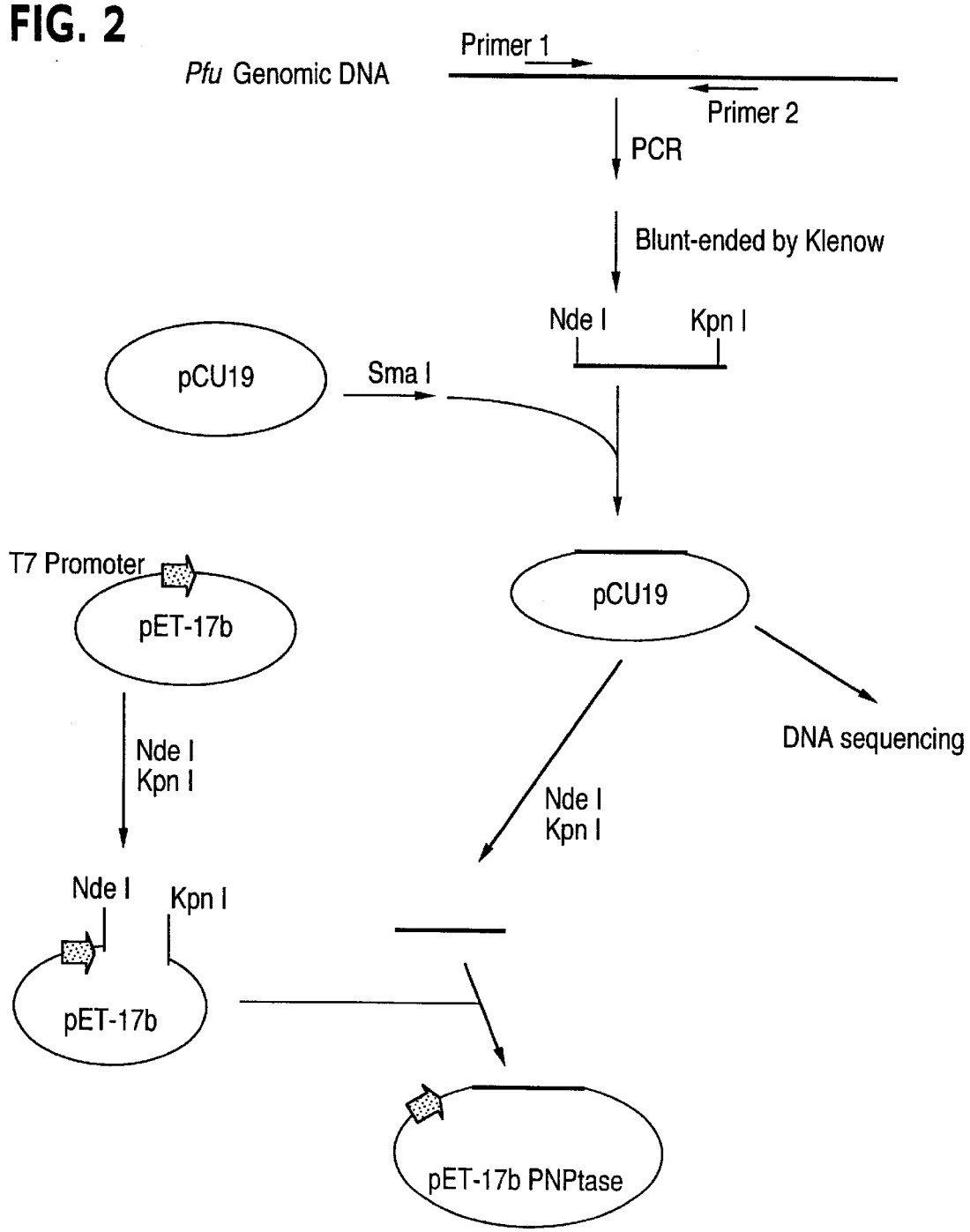
FIG. 2 is a schematic diagram illustrating the cloning of the gene encoding 3-polynucleotide phosphatase from *Pyrococcus furiosus* and the construction of the pET-17b PNPtase expression vector.

In the description that follows, a number of terms used in recombinant DNA technology are extensively utilized. In order to provide a clear and consistent understanding of the specification and claims, the following definitions are provided.

Nucleotide: As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dITP, dUTP, dGTP, dTTP, or derivatives thereof. Such derivatives include for example, (αS) dATP, 7-deaza-dGTP and 7-deaza-dATP. The term nucleotide as used herein also include dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels and enzyme labels.

Oligonucleotide: "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Gene: A DNA sequence that contains information necessary for expression of a polypeptide or protein or functional RNA. It includes the promoter and the structural gene as well as other sequences involved in expression of the protein or functional RNA.

Structural Gene: A DNA sequence that is transcribed into messenger RNA that is then translated into a sequence of amino acids characteristic of a specific polypeptide.

Substantially Pure: As used herein "substantially pure" means that the desired purified protein is essentially free from activities of contaminating enzymes which are associated with the desired protein in nature. Contaminating cellular components may include, but are no limited to, 5'-phosphatases, kinase, ligase, exonucleases, endonucleases or DNA polymerase enzymes.

"Purifying" refers herein to increasing the specific activity of an enzymatic activity over the level produced in a culture in terms of units of activity per weight of protein. This term does not imply that a protein is purified to homogeneity.

Primer: As used herein "primer" refers to a single-stranded oligonucleotide that can be extended by covalent bonding of nucleotide monomers during amplification or polymerization of a nucleic acid molecule.

Template: The term "template" as used herein refers to a double-stranded or single-stranded nucleic acid molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a template is hybridized under appropriate conditions and an appropriate polymerase may then synthesize a molecule complementary to the template or a portion thereof. The newly synthesized molecule may be equal or shorter in length than the original template.

Incorporating: The term "incorporating" as used herein means becoming a part of a nucleic acid (e.g. DNA) molecule or primer.

Amplification: As used herein "amplification" refers to any in vitro method for increasing the number of copies of a nucleic acid sequence with the use of a DNA polymerase. Nucleic acid amplification results in the incorporation of nucleotides into a DNA molecule or primer thereby forming a new DNA molecule complementary to a DNA template. The newly formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5–100 "cycles" of denaturation, annealing, and synthesis of a DNA molecule.

Polymerase Chain Reaction (PCR): The method consists of synthesizing a set of primers that have nucleotide sequences complementary to the DNA that flanks the target sequence. The primers are then mixed with a solution of the target DNA, a thermostable DNA polymerase and all four deoxynucleotides (A, T, C and G). The solution is then heated to a temperature sufficient to separate the complementary strands of DNA (approximately 95° C.) and then cooled to a temperature sufficient to allow the primers to bind to the flanking sequences. The reaction mixture is then heated again (to approximately 72° C.) to allow the DNA synthesis to proceed. After a short period of time the temperature of the reaction mixture is once again raised to a temperature sufficient to separate the newly formed double-stranded DNA, thus completing the first cycle of PCR. The reaction mixture is then cooled and the cycle is repeated.

Thermostable: As used herein "thermostable" refers to an enzyme which is resistant to inactivation by heat. The activity for a mesophilic enzyme may be inactivated by heat treatment. For example, the 3' phosphatase activity associated with T4 polynucleotide kinase is totally inactivated by exposing the enzyme to a temperature of 75° C. for one minute. As used herein, a thermostable 3' phosphatase activity is more resistant to heat inactivation than a mesophilic activity associated with other enzyme such as T4 polynucleotide kinase. However, a thermostable enzyme does not mean to refer to an enzyme which is totally resistant to heat inactivation and thus heat treatment may reduce the 3' phosphatase activity to some extent. A thermostable enzyme typically will also have a higher optimum temperature than mesophilic enzyme.

"Heterologous" refers herein to two DNA segments having different origins, i.e., not being genetically or physically linked to each other in nature. Heterologous also describes molecules that are physically or genetically linked together but which are linked together in a substantially different way than is found in nature.

"Homology," as used herein, refers to the comparison of two different nucleic acid sequences. For the present purposes, assessment of homology is as a percentage of identical bases, not including gaps introduced into the sequence to achieve good alignment. Percent homology may be estimated by nucleic acid hybridization techniques, as is well understood in the art, as well as by determining and comparing the exact base order of the two sequences. Throughout this specification, "substantial sequence homology" is meant a sequence ("A") which is capable of hybridizing to a sequence ("B") which is complementary to the invention nucleotide sequence, such that the double stranded molecule formed between A and B has a Tm within 20° C. of that of a double stranded molecule formed between B and an inventive sequence, preferably within 10° C. of each other. Calculation or measurement of the Tm of a nucleotide molecule is well known in the art.

Alternatively, substantial homology is understood that A and B hybridize under stringent conditions, at a temperature of between 50° and 70° C. in double strength SSC (2×NaCl 17.5 g/l and sodium citrate (SC) at 8.8 g/l) buffered saline containing 0.1% sodium dodecyl sulphate (SDS) followed by rinsing at the same temperature but with a buffer having a reduced SSC concentration such as single strength SSC containing 0.1% SDS, half strength SSC containing 0.1% SDS and one tenth strength SSC containing 0.1% SDS. However, optimal conditions will vary, depending on the particular hybridization reaction involved, and can be determined empirically.

A "promoter" is a nucleotide sequence upstream from the transcriptional initiation site and which contains all the regulatory regions required for transcription. Examples of promoters suitable for use in DNA constructs of the present invention include viral, fungal, bacterial, animal and plant derived promoters. The promoter may be selected from so-called constitutive promoters or inducible promoters. If a promoter is an inducible promoter, then the rate of transcription increases in response to an inducing agent. In contrast, the rate of transcription is not regulated or largely unregulated by an inducing agent, if the promoter is a constitutive promoter. Examples of constitutive promoters include the int promoter of bacteriophage, and the bla promoter of the —lactamase gene of pBR322. Examples of inducible prokaryotic promoters include the major right and left promoters of bacteriophage (Pr and Pl), trp, recA, lacZ, lacI, tet, gal, trc, and tac promoters and E. coli. The B subtilis promoters include α-amylase (Ulmanen et al., J. Bacteriol 162:176–182 (1985)) and Bacillus bateriophage promoters (Gryczan, T., In: The Molecular Biology of Bacilli, Academic Press, New York (1982)). Streptomyces promoters are described by Ward et al., Mol. Gen. Genet. 203:468478 (1986)). Prokaryotic promoters are also reviewed by Glick, J. Ind. Microbiol. 1:277–282 (1987); Cenatiempto, Y., Biochimie 68:505–516 (1986); and Gottesman, Ann. Rev. Genet. 18:415–442 (1984). Expression in a prokaryotic cell also requires the presence of a ribosomal binding site upstream of the gene-encoding sequence. Such rebosomal binding sites are disclosed, for example, by Gold et al., Ann. Rev. Microbiol. 35:365404 (1981).

A "cloning vector" is a DNA molecule, such as a plasmid, cosmid, or bacteriophage, that has the capability of replicating autonomously in a host cell. Cloning vectors typically contain a marker gene and one or a small number of restriction endonuclease recognition sites for insertion of foreign DNA sequences without affecting the essential biological function of the vector.

"Expression" is the process by which a structural gene produces a polypeptide or an RNA molecule. It includes transcription of the gene into messenger RNA (mRNA) and the translation of such mRNA into polypeptide(s).

An "expression vector" is a DNA molecule comprising a gene that is expressed in a host cell. Typically, gene expression is placed under the control of certain regulatory elements, including constitutive or inducible promoters, regulatory elements, and enhancers. As used herein, "a regulatory element" is the DNA sequence which controls or regulates the expression of the gene. Such a gene is said to be "operably linked to" or "operatively linked to" the regulatory elements, meaning that following such a link the regulatory element can direct the expression of a gene so linked thereto.

A "recombinant host" may be any prokaryotic or eukaryotic cell that contains either a cloning vector or expression vector. This term also includes those prokaryotic or eukaryotic cells that have been genetically modified.

As used herein "modified oligonuleotide with a blocking group at 3'-end" refers to a synthetic or natural oligonucleotide with a blocking group covalently linked to the oxygen atom at its 3' end. Examples of blocking groups are 3' phosphate and 3' phosphoglycolate.

The blocking group is removable by a corresponding thermostable enzyme, designated a "thermostable 3'-blocking group removing enzyme" (hereinafter "TBGRE"). As used herein, TBGRE refers to a native or modified enzyme that can efficiently remove the 3' blocking group at temperature at above about 38° C. Examples of TBGRE inlcude 3'-polynucleotide phosphatase and 3' polynucleotide phosphodiesterase, which are capable of removing the 3' phosphate and 3' phosphoglycolate group, respectively. Moreover, it is generally known to a skilled artisan that certain amino acid substitutions are considered not usually affecting the activity of the resulting peptides (see e.g. determining the conserved amino acid substitutions using the BESTFIT program of the Genetic Computing Group, Madison, Wis.). Also known in the art is that two polypeptides sharing substantial sequence similarity may also share similar functions. "Similarity" between two polypeptides is determined by comparing the amino acid sequence and its conserved amino acid substitutes of one polypeptide to the sequence of a second polypeptide. Such a determination is well known in the art and can be accomplished using computer programs such as BLAST.

Other terms used in the fields of molecular and cell biology and the DNA recombination as used herein should be generally understood well by the person of ordinary skill in the applicable arts.

Method for Improved Specificity in Polynucleotide Synthesis and Improved Specificity and Sensitivity in Polymerase Chain Reaction The present invention overcomes the problem of amplification of non-target nucleic acids resulting from mispriming at ambient temperature by blocking the 3'-hydroxyl terminus of the primer with a blocking group and removing this blockage by a corresponding, thermostable, 3'-blocking group removing enzyme, which remains inactive until reaction is desired.

The method according to the present invention for improved specificity and sensitivity in polynucleotide synthesis is illustrated below with reference to FIG. 1. In (A), the extension of the conventional primer, which is mis-annealed to a non-target DNA sequence, by a DNA polymerase (indicated by Pol.) occurs at a low temperature. The newly synthesized DNA can serve as a template at high temperatures, for example, in the following PCR cycles, causing high background and low yield of specific products. In contrast, (B) shows that when a modified primer with a blocking group at its 3' end is used, the 3' blocking group prevents the extension of the mis-annealed primer at low temperatures, while the TBGRE specifically and efficiently removes the corresponding 3' blocking group at an elevated temperature, converting modified primer to conventional primer for DNA synthesis by the DNA polymerase. The combination of the functions of a modified primer and the TBGRE increases the specificity and sensitivity of PCR and PCR related techniques. The temperatures at which these events occur are indicated in the left by a vertical bar.

Prior to the instant invention, protection of the 3'-hydroxyl terminus of a primer has never been used to improve the specificity of priming in the context of the synthesis of a polynucleotide molecule.

According to a preferred embodiment of the present invention, the blocking group is a phosphate moiety and the corresponding TBGRE is a thermostable 3'-polynucleotide phosphatase. Another preferred embodiment according to the present invention uses a phosphoglycolate as the blocking group and a thermostable 3'-polynucleotide phosphodiesterase as the TBGRE.

The 3'-polynucleotide phosphatase according to the instant invention does not have any appreciable activity at a temperature below about 38° C., and remains active at temperatures higher than 95° C. The preferred temperature range for the enzyme is above 40° C., more preferably above 45° C., and still preferably 50° C., particularly preferably above 55° C., and most preferably above 60° C.

For example, the phosphate moiety at the 3' end of an oligonucleotides primer complementary to the template of DNA/RNA for DNA synthesis blocks primer extension by a reverse transcriptase (RT) or a DNA polymerase, while the thermostable 3'-polynucleotide phosphatase removes the phosphate moiety from the 3'end of the primer at certain high temperatures (for example higher than 38° C.), making the primers extendable by RT or DNA polymerase. Such a combined use of oligonucleotides with phosphate at 3' end and a thermostable 3' polynucleotide phosphatase prohibits the extension of primers that annealed to the non-specific target sequence by RT or DNA polymerase at low temperature.

The instant invention eliminates mispriming and primer oligomerization by the use of 3'-protected primers and a TBGRE. The TBGRE suitable for the instant invention does not have any appreciable activity at a temperature below about 38° C. Because only a very small amount of the TBGRE is needed according to the instant invention, the disadvantages of the use of encapsulated PCR reagents and an antibody against DNA polymerase are avoided.

These advantages are achieved by mixing primers modified at the 3'-hydroxyl terminus, a TBGRE with a thermostable DNA polymerase and/or reverse transcriptase. The modified primers are not extendable by DNA polymerase and/or reverse transcriptase, even in the presence of all needed components including dNTP and metal cofactors in the reaction mixture at any temperature. The TBGRE removes the 3' blocking group of primers at an efficient rate at temperatures higher than about 38° C., supplying desired primers for the DNA polymerase and/or reverse transcriptase.

Because the present invention method does not interfere with the process and analysis of the amplified products, it has another advantage for being particularly amenable to automation, which has always been a problem for conventional methods which use encapsulated PCR reagents, an antibody against the DNA polymerase or a modified DNA polymerase.

Thus, by providing the 3'- modified primers and a corresponding TBGRE, one can control PCR by keeping the temperature the reaction mixture at or below about 38° C. and then let the reaction proceed by raising the temperature to desired level.

The present invention further provides modified oligonucleotides with a 3'-blocking group, and a TBGREs having activity to specifically remove the blocking group from the 3' end of the oligonucleotide molecule but not from the 5' end.

3' Phosphatase Purification

Another aspect of the present invention also relates to a purified thermostable 3'-polynucleotide phosphate from the thermophilic archaebacterium *Pyrococcus furiosus* (Pfu). This thermostable 3' polynucleotide phosphatase has an apparent molecular weight of 31 kD compared with protein standard marker (Protein BenchMarker, Life Technologies, Inc. Rockville, Md.) in 4–20% SDS PAGE (Novex, Calif.), and is capable of removing the 3' phosphate moiety of primers at efficient rate at temperature higher than 38° C., preferably higher than 45° C., most preferably higher than 50° C., supplying desired primers for DNA polymerase and/or reverse transcriptase.

One unique property of the enzyme is that it has excellent activity at 74° C., and poor activity at 37° C. and lower. Thus, by lowering the temperature from 74° C. to 37° C., the enzyme activity can be switched off.

It is known that there are 3' polynucleotide phosphatase activities associated with some purified enzymes involved in the nucleic acid metabolism such as T4 polynucleotide kinase (Richardson, C. C. *The Enzymes*, edited by Boyer, P. D., Academic Press, Inc, New York, N.Y. XIV: 299–314 (1981)) and alkaline phosphatase (Maunders, M. J. *Methods in Molecular Biology*. Edited by Burrell, M. M., Humana Press, Inc., Totowa, N.J., 16:331–341 (1993)). It is proposed that specific 3' polynucleotide phosphatase may exist and may be involved in DNA damage repair (Yang, S. W., et al. *Proc. Natl. Acad. Sci. U. S. A.* 93(21):11534–9 (1996)).

Prior to the instant invention, however, it has not been reported that a specific 3' polynucleotide phosphatase existed without detectable activities of other enzymes, such as 5'-polynucleotide phosphatase activity, DNA polymerase activity, ligase activity and so on. The inventor of the present invention is the first to obtain purified 3' polynucleotide phosphatase. To achieve such purification, the following procedure was used:

1). Activity assay of the 3' phosphatase: the 3' phosphatase assay can be carried out in different ways as described (Jilani, A, et al. J. Bio. Chem. 274(34): 24176–86 (1999); Olivares M. et al J. Bio. Chem. 274(34): 23883–86 (1999)). A preferred method is described in Example 1, which allows the monitoring of many contaminating activities such as those of endonuclease, exonulease, 5' phosphatase, ligase and DNA polymerase.

2). Isolation and purification of the 3'phosphatase: Pfu cells were subjected to sonication, ammonium sulfate precipitation, and chromatography with several commercially available separation media.

3). The determination of the 3' phosphatase protein band in SDS PAGE: During the purification of the enzyme the protein profile from fractions of each chromatographic separation is analyzed by SDS-PAGE and the activity of the enzyme in the same fractions is monitored, for example, by the assay shown in FIG. 3. By carefully analyzing the protein profile and peak of enzyme activity from each chromatography the band corresponding to the enzyme activity in the SDS-PAGE is confirmed by conventional renaturing method for protein from SDS-PAGE as described (Yang, S. W., Becker, F. F., Chan, J. Y. H. J. Bio. Chem. 265:18130–34 (1990)). The relative molecular weight of the purified enzyme is determined by comparison with protein standard marker in SDS-PAGE.

Peptides Having the 3' Polynucleotide Phosphatase Activity and DNA Sequences Encoding the Same Still provided by the present invention is an isolated polypeptide having the thermostable 3'-polynucleotide phosphatase, polynucleotide molecules that encode these polypeptides, a DNA vector that comprises the isolated polynucleotide molecule, a host cell comprising the same, and a method for producing a recombinant form of the 3'-polynucleotide phosphatase using said cell.

The 3' phosphatase gene from the Pfu according to the present invention comprises 846 base pairs (e.g., SEQ ID NO:5) that encodes 281 amino acids(SEQ ID NO:6). Genbank search using the BLAST algorithm (Altschul S F. et al. *Nucleic Acids Res.* 25: 3389–4302 (1997)) revealed that SEQ ID NO:6 shares 91% and 88% identities (see FIG. 8) with a hypothetical open reading frame (Ph 1905) from *Pyrococcus horikoshii* OT3, and an ORF (Pab 1103) from *Pyrococcus abyssi,* respectively. No significant homology (above 35% identities) was found between SEQ ID NO:6 and known proteins with 3' phosphatase activity such as T4 polynucleotide kinase. Therefore, there is a high possibility that these two open reading frames (Ph 1905 and Pab 1103) also encode similar peptides as SEQ ID NO:6 that function as thermostable 3' phosphatase.

The present invention further includes polypeptides and DNA molecules coding for polypeptides, that are analogs, fragments or derivatives of SEQ ID NO:6, which differ in terms of the identity or location of one or more amino acid residues. These include deletion analogs containing less than all of the residues specified for SEQ ID NO:6, substitution analogs wherein one or more residues specified are replaced by other residues and addition analogs where in one or more amino acid residues is added to a terminal or medial portion of the polypeptide, and which retain some or all properties of naturally-occurring enzyme.

A skilled artisan would recognize how analogs, fragments and derivatives are obtained. The polypeptides of the present invention include the polypeptide of SEQ ID NO:6 as well as polypeptides which have at least 92%, similarity (preferably at least a 92% identity) to the polypeptide of SEQ ID NO:6 and more preferably at least a 95% similarity (more preferably at least a 95% identity) to the polypeptide of SEQ ID NO:6 and also include portions or fragments of such polypeptides with such fragment of the polypeptide generally containing at least 30 amino acids and more preferably at least 50 amino acids. As known in the art "similarity" between two polypeptides is determined by comparing the amino acid sequence and its conserved amino acid substitutes of one polypeptide to the sequence of a second polypeptide. Such a determination is well known in the art and can be accomplished using computer programs such as BLAST.

Fragments or portions of the polynucleotides of the present invention generally contain at least 15 nucleotides, and preferably contain at least 20 nucleotides, and more preferably contain 25 nucleotides. Fragments or portions of the polynucleotides of the present invention may be used to synthesize full-length polynucleotides of the present invention.

The sequence alignment shown in FIG. 8 provides a roadmap to a skilled artisan for determining sequence similarity and sequence identity and for analog designing. A skilled artisan will recognize from FIG. 8 which amino acid residues need be conserved and which are changeable without affecting the enzyme activity of the peptide. Moreover, it is generally known to a skilled artisan that certain amino acid substitutions are considered not usually affecting the activity of the resulting peptides (see e.g. determining the conserved amino acid substitutions using the BESTFIT program of the Genetic Computing Group, Madison, Wis.).

The present invention provides nucleotide sequences which share substantial sequence homology to the disclosed nucleotide sequences, such as SEQ ID NO:5. The instant invention also provides DNA sequences which are degenerate to SEQ ID NO:5. Degenerate DNA sequences encode the amino acid sequence of SEQ ID NO:6, but have variations in the nucleotide coding sequences.

Vectors and Cells for in vitro Expression of the 3' Polynucleotide Phosphatase

It is well known to a skilled artisan that the cloned structural gene for the 3'-phosphatase may be used to express the enzyme in a recombinant host cell. To optimize in vitro expression of the 3' phosphatase of the present invention, well known inducible or constitutive promoters may be used to express high levels of a 3' phosphatase structural gene in a recombinant host. Similarly, high copy number vectors, well known in the art, may be used to achieve high levels of expression. Vectors having an inducible high copy number may also be useful to enhance expression of the 3' phosphatase of the invention in a recombinant host.

To express the structural gene in a prokaryotic cell (such as, *E. coli, B subtilis,* Pseudomonas, etc.), it is necessary to operably link the structural gene to a functional prokaryotic promoter. The natural promoter of the 3' phosphatase gene may function in prokaryotic hosts allowing expression of the 3' phosphatase gene, and may be used to express the 3' phosphatase gene.

To enhance the expression of the 3' phosphatase of the invention in a eukaryotic cell, well known eukaryotic promoters and hosts may be used. Preferably, however, enhanced expression of the 3' phosphatase is accomplished in a prokaryotic host. The most preferred prokaryotic host for over-expressing the 3' phosphatase of the invention is *E. coli.*

Production of 3' Polynucleotide Phosphatase

The enzymes of the present invention are preferably produced by fermentation of the recombinant host containing and expressing the desired 3' phosphatase gene. However, the 3' phosphatase of the present invention may be isolated and purified from any strain which produces the 3' phosphatase of the present invention. Fragments of the 3' phosphatase having the enzyme activity are also included in the present invention. Such fragments include proteolytic fragments, and fragments fused into other peptides, and fragments.

Any nutrient that can be assimilated by a host containing the 3' phosphatase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in ATCC Catalogs and Sambrook et al., In: *Molecular Cloning, a Laboratory Manual* ($2^{nd}$ ed.), Cold Spring Harbor Laboratory Press, Cold Spring Harbor, N.Y. (1989).

Host cells producing the 3' phosphatase of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation, or centrifugation, the 3' phosphatase can be purified by standard protein purification techniques such as extraction, precipitation, chromatography, affinity chromatography, electrophoresis or the like. Assays to detect the presence of the 3' phosphatase during purification are well known in the art (see, for example, Jilani, A, et al. *J Bio. Chem.* 274(34): 24176–86 (1999); Olivares M. et al. *J. Bio. Chem.* 274(34): 23883–86 (1999); Yang, S. W., Burgin, A. B. Jr., Huizenga, B. N., Robertson, C. A., Yao ,K. C., and Nash, H. A. *Proc. Natl. Acad. Sci. U.S.A.* 93(21):11534–9 (1996)) and can be used during conventional biochemical purification methods to determine the presence of these enzymes.

Using the Thermostable 3' Phosphatase as Markers to Determine Gene Expression

In yet another aspect, this invention provides a method for determining the expression of a protein of interest which comprises: a) constructing a fusion DNA molecule containing a DNA sequence encoding the protein of interest and the DNA sequence encoding the thermostable 3'-polynucleotide phosphatase; b) inserting the fusion DNA molecule into an expression vector; c) introducing the expression vector into a suitable host cell; d) culturing the introduced cells in conditions permitting expression of the fusion protein; and e) assaying the activity of the thermostable 3' phosphatase.

Using the Thermostable 3' Phosphatase as a Reporter to Study Regulation of Gene Expression The thermostable 3' phophatase genes of the invention can be used to study gene expression regulation. For example, a cell comprising a DNA molecule having a regulatory element from a gene, other than a gene encoding Pfu 3' phosphatase may be operatively linked to a DNA sequence encoding Pfu 3' phosphatase. By assaying the 3' phosphatase one could assess the function of the regulatory element. The cell may be selected from bacterial cell, yeast cell, fungal cell, insect cell, nematode cell, plant or animal cell. Suitable animal cells include, but are not limited to Vero cells, HeLa cells, Cos cells, CV1 cells and various primary mammalian cells. In an embodiment, the bacterial cell is *Escherichia coli*.

Use the Recombinant Pfu 3' Phosphatase to Determine the Presence or Concentration of a Ligand In still another aspect, the Pfu 3' phosphatase of this invention has several potential uses as non-isotopic methods for the detection of proteins and nucleic acids. The high thermostability of the 3' phosphatase makes it useful for direct crosslinking to protein or nucleic acid probes.

Specifically, a purified recombinant Pfu 3' phosphatase or its active fragments can be used for diagnostic purposes to determine the presence or concentration of a ligand in a sample. The sample can be a fluid or tissue specimen obtained, for example, from a patient suspected of being exposed to a particular antigen or DNA fragment. Those skilled in the art will recognize that any assay capable of using an enzyme-catalyzed system can be used in the detection methods of the present invention.

According to one embodiment of the present invention, (1) a reagent-phosphatase complex is first formed via attaching a substantially pure 3' polynucleotide phosphatase or an active fragment thereof to a reagent capable of specifically binding to the ligand to be detected; (2) a sample suspected of containing the ligand is contacted with the reagent-phosphatase complex; (3) the reagent-phophatase complex that are not bound to the specific ligand is removed; (4) a detectable agent catalyzed by the 3' polynucleotide phosphatase is then contacted with the reagent-phosphatase complex; and (6) the reaction catalyzed by the 3' polynucleotide phosphatase is detected, wherein a positive reaction indicates the presence of the ligand in the sample.

The methods can also be used to determine the concentration of a ligand in the sample by relating the amount of reaction to the concentration of the ligand according to procedures well known in the art [Noya, O. and Alarcon de Noya B. *Immunol Lett* 63 (1):53–6 (1998); Walenga, J. M. and Fareed, J. *Clin Lab Med* 14 (4):709–28 (1994)). To determine the concentration of the ligand, the amount of activities of 3' phosphatase in the test can be compared to known concentrations of the ligand or to standardized measurements, such as slopes, determined from known concentrations of the ligand. For example, the antibody against specific surface protein of HIV can be conjugated with the purified recombinant 3' phosphatase or its fragment. By comparing a standard curve of the activity of the 3'phosphatase vs the known concentration of the surface protein, one can know the concentration of the surface protein of HIV in the sample.

A variety of ligands can be detected by the present methods. The ligand can be, for example, a protein or polypeptide having antigenic properties, or a nucleic acid, such as DNA or RNA.

Reagents capable of specifically binding to such ligands can be antibodies or reactive fragments of such antibodies when the ligand is an antigen or antigen-like molecule. The reagent can also be a nucleotide probe that hybridizes or binds to a specific nucleic acid, such as DNA or RNA. Such probes can be oligonucleotides that are complementary to cDNA or genomic fragments of a ligand.

Procedures for attaching enzymes to various reagents are well known in the art. Techniques for coupling enzymes to antibodies, for example, are described (Kennedy et al., Clin. Chim. Acta 70:1 (1976)), incorporated herein by reference. Reagents useful for such coupling include, for example, glutaraldehyde, p-toluene diisocyanate, various carbodiimide reagents, p-benzoquinone m-periodate, N,N'-o-phenylenediamalemide and the like. Alternatively, the multifunctional polypeptides of the present invention can be used.

The following examples are given to illustrate the present invention. It should be understood that the invention is not to be limited to the specific conditions or details described in these examples. Throughout the specification, any and all references to publicly available documents are specifically incorporated by reference.

EXAMPLE 1

3' Polynucleotide Phosphatase Activity Assay

A modified oligonucleotide with 3' phosphate was chemically synthesized (Midland Certified Reaget Company, Midland, Tex.). The oligonucleotide is comprised following seqence:

5'-GCT GCTCTGTGCATCCGAGTGG-p-3' (SEQ ID No:7)

Figure 4:
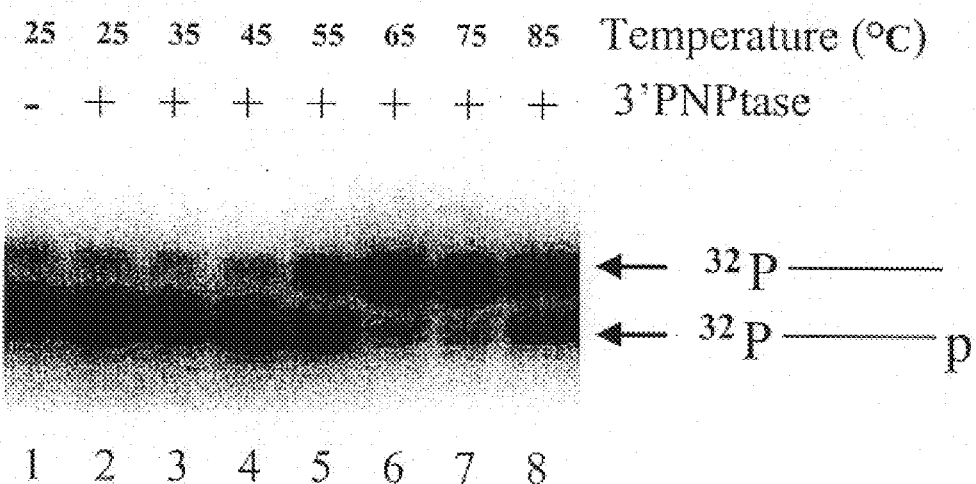
FIG. 4 is an autoradiogram showing that the *P. furiosus* 3' polynucleotide phosphatase specifically removed the 3'-phosphate moiety of an oligonucleotide in a temperature-dependent manner. The reaction mix described in Example 7 was analyzed by 16% polyacrylamide-7 M urea gel electrophoresis. The oligonucleotide with a phosphate at the 3' end migrates faster than one without a phosphate (arrows).

The Oligonucleotide was labeled with $^{32}P$ at 5' end by T4 polynucleotide kinase that lacks 3' polynucleotide phosphatase as described (Yang, S. W., et al. *Proc. Natl. Acad. Sci. U. S. A.* 93(21):11534–9 (1996)). The $^{32}P$ labeled substrates were incubated with purified 3' polynucleotide phosphatase in 1×PCR reaction buffer 10 mM Tris-HCl, pH 8.3, 50 mM KCl, 2.5 mM MgCl$_2$ at 72° C. for 5 minutes. After addition of DNA sequencing buffer and heating at 90° C. for 2 minutes, the samples were analyzed by 12% polyacrylamide-7 M urea gel electrophoresis. The radioactivities in the substrate and products as shown in FIG. 4 were quantitated with a PhophorImager (Molecular Dynamics). One unit of 3' phosphatase is defined that the among of the enzyme is required to remove 5 μmol of 3'end phosphate from polynucleotide in 5 min.

EXAMPLE 2
Isolation and Purification 3' Phosphatase from Pfu

One hundred grams of wet Pfu cells (purchased from the Center of Marine Biotechnology, University of Maryland, Baltimore, Md.) were resuspended in ice cold disruption buffer, 20 mM Tris-HCl, pH 7.5, 1 mM EDTA, 1 mM DTT, 0.2 M NaCl, 10 mM mercaptoethanol, and 2 mM phenyl-methylsulfonyl fluoride. Next, cells were lysed by sonication, and centrifuged in a Sorvall GS-3 rotor at 8,200 rpm for 10 min. To the supernatant was added 0.05 vol of a 10% solution of polyethyleneimine . After stirring and centrifugation the supernatant was fractionated with ammonium sulfate (45–80% saturation). The resulting sample were subjected to chromatography through a Phosphocellulose (P-11; Whatman, Inc.; activity eluted ≈0.6 M NaCl), Source 15S (Pharmacia; activity eluted≈0.2 M NaCl), double-stranded DNA-cellulose (Sigma; activity eluted≈0.15 M NaCl), and Mono S column (Pharmacia; activity eluted≈0.35 M NaCl), Heparin-Sepharose (Pharmacia: activity eluted≈0.3 M NaCl), MonoQ column (Pharmacia; activity eluted≈0.25 M NaCl) and the enzyme was concentrated with a MonoS column (Pharmacia). The location of the 3' phosphatase on the SDS-PAGE was determined by a renaturizing the protein excised from SDS-PAGE as described (Yang, S. W., et al. *Proc. Natl. Acad. Sci. U. S. A.* 93(21):11534–9 (1996)). The purified 3' phosphatase has relative molecular weight about 31 KD when analyzed by 4–20% SDS-PAGE Compared with standard Protein Marker (Life Technologies, Inc).

EXAMPLE 3
Sequencing of N-terminal Peptide of the 3' Phosphatase

The partially purified 3' phosphatase was subjected to 7% SDS-Tricine PAGE. The proteins on the SDS gel were transferred to a PVDF membrane (Immobolin-P from Millipore) by electrophoresis in transfer buffer (0.5×TBE (pH 8.4), 20% methanol, 0.5 mM EDTA) for 1 hr at 0.5 A current. The membrane was stained with Coomassie blue R-250 for 10 min and then destained with 100% methanol twice. The band corresponding to the 3' phosphatase on the membrane was excised. The amino acid sequencing was carried out by the commercial service facility at Yale University. The 27 amino acid sequence is lised in a single letter symbol starting from N-terminus as following:

FKIDRLRFGTAGIPLSTPKPSTIAGI (SEQ ID NO: 1).

EXAMPLE 4
Cloning the Gene Encoding the 3' Phosphatase from the Pfu Genomic DNA The cloning of the 3' phosphatase is outlined in FIG. 2 and briefly described as following: the N-terminal amino acid sequence (SEQ ID NO: 1) was used to search Genbank using the BLAST algorithm (Altschul SF. et al. Nucleic Acids Res. 25: 3389–4302 (1997)). The search produced two alignments with 96% amino acid identities. One of the identified sequences is a part of a hypothetical open reading frame (Ph 1905) from *Pyrococcus horikoshii* OT3, and the other is a part of a hypothetical open reading frame(Pab 1103) from *Pyrococcus abyssi*. The two open reading frames both contain a C-terminal fragment 23 amino acids in length having identical amino acid sequences:

ISESPNIEGDAILMKKKWEELKI (SEQ ID NO:2).

No significant homology (above 35% of identities) was found between SEQ ID NO:1 and known proteins with 3' phosphatase activity.

In order to clone the thermostable 3' phasphatase gene, the inventor of the present invention, based upon SEQ ID NO:1 and SEQ ID NO:2, designed and chemically synthesized a pair of primers (SEQ ID NO:3 and SEQ ID NO:4):

Primer 1:
5'-GGAATTCGACATATGTTTAAAATAGACAGGC TAAGATTTGG (SEQ ID NO:3)

Primer 2:
5'-GGTACCTTAAATTTTTAGCTCTTCCCACTTTTT (SEQ ID NO:4).

The restriction enzyme recognition sequences for Nde I and Kpn I flanks the 5' end of primer 1 and primer 2, respectively. These primers were used in the PCR mixture containing the Pfu genomic DNA as template and the Pfu DNA polymerase according to the instruction of the manufacturer (Stratagene Inc., Calif.). The synthesized DNA fragment was purified by 1% agrose gel electrophoresis. After their 3' end was blunted and 5' end dephosphoryllated by conventional methods as described (Sambrook et al. in: Molecular Cloning, A Laboratory Manual (2$^{nd}$ Ed.) Cold Spring Harbor Laboratory Press, Cold Spring Harbor, N.Y. (1989)) the fragment was ligated into the plasmid vector pUC19. The plasmid (pUC19-PNPtase) containing the DNA fragment was recovered from the clone strain *E. coli* DH5α and DNA sequence (SEQ ID NO:5) for the fragment was determined by conventional method (PE Applied Biosystems). Further, the amino acid sequence (SEQ ID NO:6) was deduced from the determined DNA sequence. The 3' phosphatase gene derived from Pfu strain comprised 846 bases wherein 281 amino acids were encoded. Upon comparison with the other two hypothetical open reading frames mentioned above, the amino acid sequence of 3' phosphatase from Pfu in the present invention shares 91% and 88% identities with Ph 1905 and Pab 1103, respectively (see FIG. 8). Therefore, there is a high possibility that these two open reading frames may also encoding similar peptides as SEQ ID NO:6 that function as thermostable 3' phosphatase.

EXAMPLE 5
Construction of Recombinant Expression Vector

In order to express and purify recombinant 3' phosphatase, the plasmid DNA (pUC19-PNPtase) was digested with Nde I and Kpn I. The DNA fragment containing the 3' phosphatase gene was purified by 1% agrose gel electrophoresis and ligated into the *E. coli* expression vector pET-17b (Novagen, Calif.) to create pET-17b-PNPtase. The ligation mixture was used to transform the *E. coli* DH5α cells. The correct clone was selected by PCR with primer 1 and primer 2. The sequence of the 3' phosphatase gene in pET-17b-PNPtase was determined again as mentioned above.

EXAMPLE 6
Expression and Purification of the Recombinant 3' Phosphatase Derived from Pfu

Figure 3:
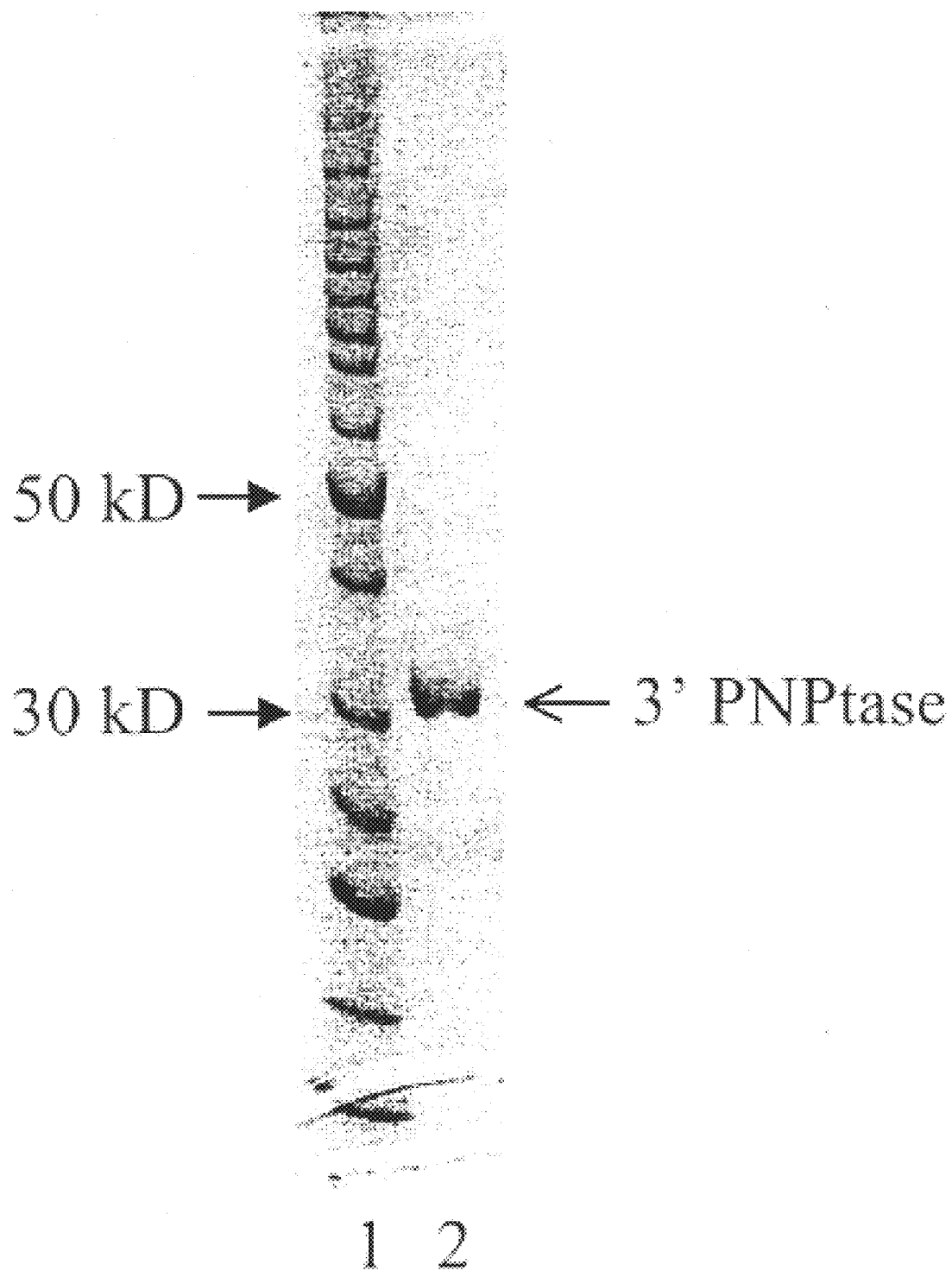
FIG. 3 is a polyacrylaminde-SDS gel electrophoresis analysis of the recombinant *P. furiosus* 3' polynucleotide phosphatase purified by last step chromatography through a Mono Q column (HR 5/5, Pharmacia Biotech).

*Escherichia coli* (BL21(DE3)) was transformed using the recombinant expression vector (pET-17b-PNPtase) obtained in Example 5. The resulting transformant was cultured in a LB medium. Three hours before collecting the bacterial cells, an induction treatment was conducted by addition of isopropylthio-β-D-galactopyranoside(IPTG). Bacterial cells were recovered from the cultural medium by centrifugation. The cells were resuspended in a buffer and disintegrated by an untrasonic treatment. The cell extract was heated at 76° C. for 20 min. After cooling in ice-water for 10 min, polyethyleneimine was added to the extract. The supernatant was recovered and ammonium precipitation (45–80% saturation) was performed as above. The resulting pellet was resuspended in buffer R (20 mM Tris-HCl, pH 7.5, 1 mM EDTA, 1 mM DTT, 0.2 M NaCl, 10 mM mercaptoethanol). After a brief centrifugation, the sample was subjected to chromatography through a Hydroxylapatite (BioRad) column and the 3' phosphatase was eluted with a gradient of 1 mM to 400 mM phosphate in buffer R. The fractions containing the 3' phosphatase were further processed through Mono S and Mono Q column as mentioned above. The purified 3' phosphatase as shown in FIG. 3 does not contain detectable activities of exonulease, DNA ligase, polynucleotide kinase, DNA polymerase, proteinase, or 5' polynucleotide phosphatase that may interfere with a PCR reaction (data not shown).

EXAMPLE 7

Specific Removal of the Phosphate at 3' End of Oligonucleotide by the Recombinant 3' Phosphatase Oligonucleotides (SEQ ID No.7) with phosphate at the 3'end were labeled with $^{32}$P labeled at the 5' end by T4 polynucleotide kinase that lacks 3' polynucleotide phosphatase as described (Yang, S. W., et al. *Proc. Natl. Acad. Sci. U. S. A.* 93(21):11534–9 (1996)). The $^{32}$P labeled substrates were incubated with the purified recombinant 3' phosphatase in 1×PCR buffer (10 mM Tris-HCl, pH 8.3, 50 mM KCl, 2.5 mM MgCl$_2$) at the desired temperature for 5 min. After addition of DNA sequencing buffer and heating at 90° C. for 2 minutes, the samples were analyzed by 12% polyacrylamide-7 M urea gel electrophoresis.

EXAMPLE 8

Thermostable 3' Phosphatase-dependent Extension of Modified Oligonucleotide Primers by Taq and Pfu DNA Polymerases A $^{32}$P labeled oligonucleotide with 3' end phosphate blocking group (SEQ ID No:7) annealed to its complementary template
5'-AACCTCGTAACCTTCGGTACACTCGGATG CACAGAGCAGC-3' (SEQ ID NO:8)
and Taq or Pfu DNA polymerase were incubated with or without the purified recombinant 3' phosphatase at 68° C. for 30 seconds and 10 minutes, respectively. After addition of DNA sequencing buffer and heating at 90° C. for 2 minutes, the samples were then assayed by 12% polyacrylamide-7 M urea gel electrophoresis.

When the purified recombinant enzyme was incubated with the modified oligonucleotide primers in the PCR reaction mixture, it specifically removed the phosphate moiety from 3' end of the primer but not from the 5' end (see FIG. 4). In comparison, the thermostable alkaline phosphatase derivatived from Tth (Szasz, J., and Davis, M., U.S. Pat. No. 5,939,257 (1999)) failed to be used in the present invention to increase the sensitivity and specificity of DNA amplification because it contains both 3' and 5' phosphatase activities. The 5' phosphatase destroys the deoxynucleosidetriphosphates (termed dNTP including dATP, dTTP, dCTP and dGTP), the substrates that a thermostable DNA polymerase uses to synthesize DNA in PCR.

As shown in FIG. 4, the purified enzyme has a maximum activity within the temperature range from 55° C.–80° C. that is also the optimal region of temperature for all thermostable DNA polymerases used for DNA amplification in PCR and PCR related techniques.

Figure 5:
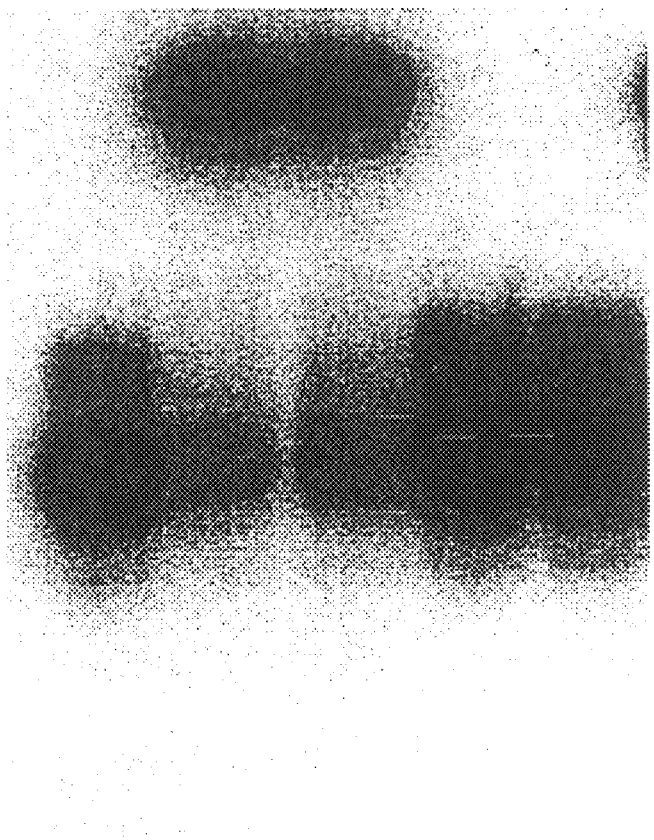
FIG. 5 is an autoradiogram showing that primer extension depends on the recombinant *P. furiosus* 3' polynucleotide phosphatase as described in the Example 8, wherein the 5'-$^{32}$P labeled primer is blocked with a phosphate at the 3' end.

The modified primer with a phosphate at the 3' end is stable at 68° C. for 10 min in the absence of the recombinant 3' phosphatase in the reaction mixture in this experiment (FIG. 5, lanes 4 and 5). The absence of any extended product in these two lanes indicates that the 3' phosphate moiety of the primers is stable at 68° C. and resists the 3' exonuclease associated with Pfu DNA polymerase, blocking their extension by Taq and Pfu DNA polymerases. However, in the same reaction mixture, together with the purified recombinant 3' polynucleotide phosphatase, almost all of the 20 pmol of the modified primers, the amount of primers used in routine PCR, were extended within 30 seconds at 68° C. (FIG. 5, lanes 2 and 3). These results prove that the 3' phosphatase removes phosphate from 3' end of primers in a very efficient way so that all of the modified primers can be converted to conventional primers in the initial cycle without the requirement for an additional pause. Further study showed that the modified primer with 3' end phosphate can survive for many weeks in the complete PCR mixture without the 3' phosphatase at room temperetue and 5 days at 68° C. as we tested (data not shown).

EXAMPLE 9

Increasing Specificity in the PCR to Amplify DNA Fragments by Using Modified Primers and the 3' Phosphatase In order to amplify a DNA fragment of the human β-globin gene, a pair of primers was selected from a region of the human β-globin gene (Collins, F. S. and Weissman, S. M. *Prog Nucleic Acid Res Mol Biol* 31:315–462 (1984)) was chemically synthesized with or without phosphate at the 3' ends and expected to yield PCR products with length of 2.8 kb:

Primer 3: 5'-GCT GCTCTGTGCATCCGAGTGG-p-3' (SEQ ID NO:7) and

Primer 4: 5'-CCAGGATTTTTGATGGGACACG-p-3' (SEQ ID NO:9)

The purified recombinant 3'phosphatase together with Taq DNA polymerase or Pfu DNA polymerase in the PCR mixtures (10 mM Tris-HCl, pH 8.3, 50 mM KCl, 2.5 mM MgCl$_2$, 200 µM dNTP) in which a serial diluted human genomic DNA -was used as template. The PCR was performed as: 94° C. for 2 min followed by 30 cycles of 55° C. 15 seconds, 72° C. 3 minutes and 94° C. for –15 seconds. These PCR products were subjected to an agarose gel electrophoresis. The control experiment was carried out in the same PCR conditions except that the 3' phosphatase was omitted in the reaction and conventional primers with the same sequence as modified primers were used:

Primer 5: 5'-GCTGCTCTGTGCATCCGAGTGG-3' (SEQ ID NO:10) and

Primer 6: 5'-CCAGGATTTTTGATGGGACACG-3' (SEQ ID NO:11).

The result is shown in FIG. 6.

EXAMPLE 10

Increasing Sensitivity in PCR to Amplify DNA Fragments by Using Modified Primers and the 3' Phosphatase A pair of conventional oligonucleotides complementary to the gag gene sequences 1551–1578 and 1638–1665, termed SK38 and SK39, respectively, have been used to amplify the a 115 bp DNA fragment for direct detection HIV-1 in peripheral blood mononuclear cells (Ou, C. Y. et al, *Science* 239(4837):295–7 (1988)). The gag gene of HIV-1 was inserted into a plasmid vector pUC19 to construct pUC19-gag to be used as template. The SK38 and SK39 primers with phosphate at their 3' ends were chemically synthesized:

Primer 7:
5'-ATAATCCACCTATCCCAGTAGGAGAAAT-p-3' (SEQ ID NO:12) and

Primer 8:
5'-TTTGGTCCTTGTCTTATGTCCAGAATGC-p-3' (SEQ ID NO:13)

The purified recombinant 3' phosphatase and primers 7 and 8 was used in the PCR to amplify the 115 bp fragment by Taq DNA polymerase. The PCR mixture as described in the Example 9 contains a serial dilution of gag gene templates (pUC19-gag) and 200 ng of human genomic DNA as nonspecific-target. The PCR was performed as: 94° C. for 2 min followed by 40 cycles of 55° C. 15 seconds, 72° C. 3 minutes and 94° C. for 15 seconds. The products of the reaction were analyzed by agarose gel electrophoresis. For the control experiment, the 3' phosphatase was omitted in the same PCR reaction and conventional SK38 and SK39 primers were used:

Primer 9: 5'-ATAATCCACCTATCCCAGTAGGAGAAAT-3' (SEQ ID No. 14) and

Primer 10: 5'-TTTGGTCCTTGTCTTATGTCCAGAATGC-3' (SEQ ID No.15).

The result is shown in FIG. 7.

I claim:

1. A method for selectively amplifying a target polynucleotide molecule, comprising:
   (A) contacting a specimen suspected of containing said target polynucleotide molecule with a reaction mixture comprising (1) a primer complementary to said target polynucleotide molecule, wherein the 3'-hydroxyl terminus of the primer is protected with a blocking group that prevents chain-elongation; (2) a thermostable blocking group removing enzyme (TBGRE); (3) a thermostable polynucleotide polymerase; (4) at least one nucleoside-5'-triphosphate; and
   (B) elevating the temperature of the resulting mixture to higher than about 38° C., thereby generating a primer extension product.

2. The method of claim 1, further comprising the step of
   C. denaturing the primer extension product and conducting at least one additional primer extension reaction.

3. The method of claim 2 wherein said primer extension reaction is part of a polymerase chain reaction (PCR) cycle.

4. The method according to claim 3, wherein the primer extension product is detected after the last PCR cycle by detecting the presence of said target nucleic acid in said specimen.

5. The method of claim 1 wherein the thermostable polynucleotide polymerase is a DNA polymerase or a reverse transcriptase.

6. The method of claim 1, wherein the blocking group is a 3'-phosphate moiety and the TBGRE is a 3'-polynucleotide phosphatase.

7. The method of claim 6, wherein the 3' polynucleotide phosphatase is isolated from a thermophilic archaebacterium.

8. The method of claim 7, wherein the thermophilic archaebacterium is *Pyrococcus furiosus*.

9. The method according to claim 1, wherein the blocking group is a 3'-phosphoglycolate and the TBGRE is a 3'-polynucleotide phosphodiesterase.

10. A kit comprising (1) an oligonucleotide primer capable of hybridizing to a template nucleic acid molecule, the 3'-hydroxyl terminus of said primer is protected with a blocking group; (2) a thermostable enzyme capable of removing said blocking group; (3) a reverse transcriptase or DNA polymerase or both; and (4) at least one nucleotide 5'-triphosphate.

11. The kit according to claim 10 wherein the blocking group is a 3'-phosphate moiety and the thermostable enzyme is a 3'-polynucleotide phosphatase.

12. The kit according to claim 10 wherein the blocking group is a 3'-phosphoglycolate and the thermostable enzyme is a 3'-polynucleotide phosphodiesterase.

13. The method of claim 1, wherein the TBGRE is encoded by a DNA molecule comprising the nucleotide sequence of SEQ ID NO:5.

14. The method of claim 1, wherein the TBGRE comprises the amino acid sequence of SEQ ID NO:6.

15. The kit of claim 11, wherein the TBGRE is encoded by a DNA molecule comprising the nucleotide sequence of SEQ ID NO:5.

* * * * *

SEQUENCE LISTING

<160> NUMBER OF SEQ ID NOS: 17

<210> SEQ ID NO 1
<211> LENGTH: 26
<212> TYPE: PRT
<213> ORGANISM: Pyrococcus furiosus

<400> SEQUENCE: 1

Phe Lys Ile Asp Arg Leu Arg Phe Gly Thr Ala Gly Ile Pro Leu Ser
 1               5                  10                  15

Thr Pro Lys Pro Ser Thr Ile Ala Gly Ile
            20                  25

<210> SEQ ID NO 2
<211> LENGTH: 23
<212> TYPE: PRT
<213> ORGANISM: Pyrococcus furiosus

<400> SEQUENCE: 2

Ile Ser Glu Ser Pro Asn Ile Glu Gly Asp Ala Ile Leu Met Lys Lys
 1               5                  10                  15

Lys Trp Glu Glu Leu Lys Ile
            20

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 3
ggaattcgac atatgtttaa aatagacagg ctaagatttg g                    41

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 4
ggtaccttaa atttttagct cttcccactt ttt                             33

<210> SEQ ID NO 5
<211> LENGTH: 846
<212> TYPE: DNA
<213> ORGANISM: Pyrococcus furiosus -continued

<400> SEQUENCE: 5

```
atgtttaaaa tagacaggct aagatttgga actgctggaa tacctctttc tactccaaaa      60
ccttctacaa tagctggaat tgaaagggtt agagagcttg actagatgc catggagctt      120
gaatttgtga gaggagtaaa tataaggccc gaactggcaa agaaaataaa atacgtagca      180
aaaaagaacg acgttgtttt aacagcgcat gccccatact acataaactt aaacgccaaa      240
gagaaggaaa agtgaaag tagcaaaagg agaattattc agagtgcaga aaggctatat      300
gaggcaggag gatggagcgt agtttttcat gctggctatt acttgaaaga acatccagaa      360
aaggtttatc agaaaattga agcacacta aaggatatag agagagaatt aaaggacagg      420
ggaatagaag tctggctgag acctgagttg acgggaaagc cgacccaatt tggagatctg      480
aaagaattaa ttaaattaag tcaaaaccta gagcttgttc ttcccgcaat agactttgcc      540
catgcccatg cgaggaataa gggaaagtgt aactctgaag aagagtggag agagatgcta      600
gctttaattg aaaacgagct tgggagagag gcattagata acatgcatat tcacataagt      660
ggaattgaat acacagaaaa gggagaaaag aggcatctca atctagagga gagcgatctt      720
aaatgggaag atctactcaa agttctcaaa gaatttaaag ttaagggcgt tgtaataagt      780
gagagcccca atatagaagg ggatgctctg cttatgaaga aaaagtggga agagctaaaa      840
atttaa                                                                846
```

<210> SEQ ID NO 6
<211> LENGTH: 281
<212> TYPE: PRT
<213> ORGANISM: Pyrococcus furiosus

<400> SEQUENCE: 6

```
Met Phe Lys Ile Asp Arg Leu Arg Phe Gly Thr Ala Gly Ile Pro Leu
  1               5                  10                  15

Ser Thr Pro Lys Pro Ser Thr Ile Ala Gly Ile Glu Arg Val Arg Glu
             20                  25                  30

Leu Gly Leu Asp Ala Met Glu Leu Glu Phe Val Arg Gly Val Asn Ile
         35                  40                  45

Arg Pro Glu Leu Ala Lys Lys Ile Lys Tyr Val Ala Lys Lys Asn Asp
     50                  55                  60

Val Val Leu Thr Ala His Ala Pro Tyr Tyr Ile Asn Leu Asn Ala Lys
 65                  70                  75                  80

Glu Lys Glu Lys Val Glu Ser Ser Lys Arg Ile Ile Gln Ser Ala
             85                  90                  95

Glu Arg Leu Tyr Glu Ala Gly Gly Trp Ser Val Phe His Ala Gly
        100                 105                 110

Tyr Tyr Leu Lys Glu His Pro Glu Lys Val Tyr Gln Lys Ile Glu Ser
        115                 120                 125

Thr Leu Lys Asp Ile Glu Arg Glu Leu Lys Asp Arg Gly Ile Glu Val
    130                 135                 140

Trp Leu Arg Pro Glu Leu Thr Gly Lys Pro Thr Gln Phe Gly Asp Leu
145                 150                 155                 160

Lys Glu Leu Ile Lys Leu Ser Gln Asn Leu Glu Leu Val Leu Pro Ala
                165                 170                 175

Ile Asp Phe Ala His Ala His Ala Arg Asn Lys Gly Lys Cys Asn Ser
            180                 185                 190

Glu Glu Glu Trp Arg Glu Met Leu Ala Leu Ile Glu Asn Glu Leu Gly
        195                 200                 205
```

```
Arg Glu Ala Leu Asp Asn Met His Ile His Ile Ser Gly Ile Glu Tyr
        210                 215                 220

Thr Glu Lys Gly Glu Lys Arg His Leu Asn Leu Glu Glu Ser Asp Leu
225                 230                 235                 240

Lys Trp Glu Asp Leu Leu Lys Val Leu Lys Glu Phe Lys Val Lys Gly
                245                 250                 255

Val Val Ile Ser Glu Ser Pro Asn Ile Glu Gly Asp Ala Leu Leu Met
            260                 265                 270

Lys Lys Lys Trp Glu Glu Leu Lys Ile
            275                 280

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: modified
      oligonucleotide with 3' phosphate

<400> SEQUENCE: 7
gctgctctgt gcatccgagt gg                                              22

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
aacctcgtaa ccttcggtac actcggatgc acagagcagc                           40

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
ccaggatttt tgatgggaca cg                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
gctgctctgt gcatccgagt gg                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ccaggatttt tgatgggaca cg                                              22
```

-continued

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
ataatccacc tatcccagta ggagaaat                              28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 13
tttggtcctt gtcttatgtc cagaatgc                              28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 14
ataatccacc tatcccagta ggagaaat                              28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 15
tttggtcctt gtcttatgtc cagaatgc                              28

<210> SEQ ID NO 16
<211> LENGTH: 281
<212> TYPE: PRT
<213> ORGANISM: Pyrococcus horikoshii

<400> SEQUENCE: 16

Met Phe Lys Ile Asp Arg Leu Arg Phe Gly Thr Ala Gly Ile Pro Ile
 1               5                  10                  15

Ser Thr Pro Lys Pro Ser Thr Ile Ala Gly Ile Glu Arg Val Arg Glu
            20                  25                  30

Leu Gly Leu Asp Ala Met Glu Leu Glu Phe Val Arg Gly Ile Asn Ile
        35                  40                  45

Lys Pro Glu Leu Ala Lys Lys Ile Lys Tyr Val Ala Glu Lys Asn Asp
    50                  55                  60

Ile Val Leu Thr Ala His Ala Pro Tyr Tyr Ile Asn Leu Asn Ala Lys
65                  70                  75                  80

Glu Lys Glu Lys Val Glu Ala Ser Lys Arg Arg Ile Ile Gln Ser Ala
                85                  90                  95

Glu Arg Leu Tyr Glu Ala Gly Gly Trp Ser Val Val Phe His Ala Gly
            100                 105                 110

Tyr Tyr Leu Lys Gln Pro Lys Glu Ser Val Tyr Gln Lys Ile Leu Ser
        115                 120                 125

```
Ala Leu Lys Glu Ile Gln Lys Glu Leu Met Asp Lys Gly Ile Lys Val
    130                 135                 140

Trp Leu Arg Pro Glu Leu Thr Gly Lys Pro Thr Gln Phe Gly Asp Leu
145                 150                 155                 160

Lys Glu Leu Val Lys Leu Ser Gln Glu Leu Glu Leu Val Leu Pro Ala
                165                 170                 175

Ile Asp Phe Ala His Ala His Ala Arg Asn Lys Gly Lys Cys Asn Thr
            180                 185                 190

Glu Glu Glu Trp Arg Glu Met Leu Ala Leu Ile Glu Asn Glu Leu Gly
                195                 200                 205

Arg Glu Ala Leu Asp Asn Met His Ile His Ile Ser Gly Ile Glu Tyr
210                 215                 220

Gly Glu Lys Gly Glu Lys Arg His Leu Asn Leu Glu Ser Asp Leu
225                 230                 235                 240

Lys Trp Glu Asp Leu Leu Lys Val Leu Lys Glu Phe Arg Val Lys Gly
                245                 250                 255

Val Ile Ile Ser Glu Ser Pro Asn Ile Glu Gly Asp Ala Ile Leu Met
                260                 265                 270

Lys Lys Lys Trp Glu Glu Leu Lys Ile
                275                 280
```

<210> SEQ ID NO 17
<211> LENGTH: 281
<212> TYPE: PRT
<213> ORGANISM: Pyrococcus abyssi

<400> SEQUENCE: 17

```
Met Phe Lys Ile Asp Arg Leu Arg Phe Gly Thr Ala Gly Ile Pro Ile
1               5                   10                  15

Ser Thr Pro Lys Pro Ser Thr Ile Ala Gly Ile Glu Arg Val Arg Glu
                20                  25                  30

Leu Gly Leu Asp Ala Met Glu Leu Glu Phe Val Arg Gly Ile Asn Ile
            35                  40                  45

Lys Pro Glu Leu Ala Lys Lys Ile Lys His Val Ala Lys Lys Asn Asp
    50                  55                  60

Val Val Leu Thr Ala His Ala Pro Tyr Tyr Ile Asn Leu Asn Ala Lys
65                  70                  75                  80

Glu Lys Glu Lys Val Glu Ala Ser Lys Arg Arg Ile Ile Gln Ser Ala
                85                  90                  95

Glu Arg Leu Tyr Glu Ala Gly Gly Trp Ser Leu Val Phe His Ala Gly
            100                 105                 110

Tyr Tyr Leu Lys Gln Pro Pro Glu Leu Val Tyr Glu Arg Ile Lys Ser
        115                 120                 125

Glu Leu Lys Asp Ile Glu Lys Glu Leu Leu Asp Arg Gly Ile Lys Val
    130                 135                 140

Trp Ile Arg Pro Glu Leu Thr Gly Lys Pro Thr Gln Phe Gly Asn Leu
145                 150                 155                 160

Met Glu Leu Ile Arg Leu Ser Gln Asp Leu Glu Leu Val Leu Pro Ala
                165                 170                 175

Ile Asp Phe Ala His Ala His Ala Arg Asn Lys Gly Lys Cys Asn Ser
            180                 185                 190

Glu Glu Glu Trp Arg Glu Met Leu Thr Leu Ile Glu Lys Glu Leu Gly
                195                 200                 205

Arg Glu Ala Leu Asp Asn Met His Ile His Ile Ser Gly Ile Glu Tyr
210                 215                 220
```

```
Ser Asp Lys Gly Glu Lys Arg His Leu Asn Leu Gln Glu Ser Asp Met
225                 230                 235                 240

Arg Trp Glu Glu Leu Leu Lys Thr Leu Lys Glu Phe Lys Val Lys Gly
                245                 250                 255

Val Val Ile Ser Glu Ser Pro Asn Ile Glu Gly Asp Ala Ile Leu Met
            260             265                 270

Lys Lys Lys Trp Glu Glu Leu Lys Ile
        275             280
```